(12) United States Patent
DeVries et al.

(10) Patent No.: US 11,273,292 B2
(45) Date of Patent: Mar. 15, 2022

(54) AUTOLOGOUS PLEURODESIS METHODS AND DEVICES

(71) Applicant: Carefusion 2200, Inc., San Diego, CA (US)

(72) Inventors: Elise DeVries, Chicago, IL (US); John Krueger, Muskego, WI (US); Shayna Massi, Chicago, IL (US); John Ray, Indian Creek, IL (US); Palak Doshi, Winfield, IL (US)

(73) Assignee: Carefusion 2200, Inc., San Diego, CA (US)

( * ) Notice: Subject to any disclaimer, the term of this patent is extended or adjusted under 35 U.S.C. 154(b) by 196 days.

(21) Appl. No.: 16/243,569

(22) Filed: Jan. 9, 2019

(65) Prior Publication Data

US 2019/0143083 A1 May 16, 2019

Related U.S. Application Data

(63) Continuation of application No. 15/610,381, filed on May 31, 2017, now Pat. No. 10,207,082, which is a
(Continued)

(51) Int. Cl.
*A61M 25/06* (2006.01)
*A61M 25/00* (2006.01)
(Continued)

(52) U.S. Cl.
CPC ......... *A61M 25/0662* (2013.01); *A61B 90/39* (2016.02); *A61M 25/007* (2013.01);
(Continued)

(58) Field of Classification Search
CPC ......... A61M 25/0662; A61M 25/0041; A61M 25/0045; A61M 25/007; A61M 25/0108; A61M 25/0606; A61B 90/39
(Continued)

(56) References Cited

U.S. PATENT DOCUMENTS

| 4,850,955 A | 7/1989 | Newkirk |
| 5,279,551 A | 1/1994 | James |
| 5,286,254 A | 2/1994 | Shapland et al. |
| 5,312,331 A | 5/1994 | Knoepfler |

(Continued)

FOREIGN PATENT DOCUMENTS

| EP | 1475117 A2 | 11/2004 |
| EP | 1649880 A2 | 4/2006 |

(Continued)

OTHER PUBLICATIONS

CareFusion PleurX catheter system, Product Brochure, © 2010, 4 paqes.
(Continued)

*Primary Examiner* — Phillip A Gray
(74) *Attorney, Agent, or Firm* — Dinsmore & Shohl LLP

(57) ABSTRACT

System and components for inducing pleurodesis or other sclerosis or desired adhesion conditions to treat a patient, while minimizing likelihood of tissue damage from direct application of sclerosis-enhancing materials. A tube device is provided that is configured to elute sclerosis-enhancing material and/or other medicaments including autologous or otherwise patient compatible blood and/or blood component(s) via an assembly including fenestrated drainage tube which may be a multi-lumen assembly allowing simultaneous infusion/elution and drainage. The assembly of tube device with outer (typically drainage) tube may include one or more features configured to enhance delivery of medicament and/or drainage through the same assembly.

14 Claims, 6 Drawing Sheets

Related U.S. Application Data continuation of application No. 14/139,008, filed on Dec. 23, 2013, now Pat. No. 9,682,218.

(51) Int. Cl.
 *A61M 25/01* (2006.01)
 *A61B 90/00* (2016.01)

(52) U.S. Cl.
 CPC .... *A61M 25/0041* (2013.01); *A61M 25/0045* (2013.01); *A61M 25/0108* (2013.01); *A61M 25/0606* (2013.01); *A61B 2090/3925* (2016.02); *A61B 2090/3954* (2016.02); *A61B 2090/3966* (2016.02); *A61M 25/0032* (2013.01); *A61M 25/0102* (2013.01); *A61M 2025/0036* (2013.01); *A61M 2025/0681* (2013.01); *A61M 2205/0266* (2013.01)

(58) Field of Classification Search
 USPC .......................................................... 604/506
 See application file for complete search history.

(56) References Cited

U.S. PATENT DOCUMENTS

| | | | |
|---|---|---|---|
| 5,484,401 | A | 1/1996 | Rodriquez et al. |
| 5,741,248 | A | 4/1998 | Stern et al. |
| 6,302,870 | B1 | 10/2001 | Jacobsen |
| 6,719,749 | B1* | 4/2004 | Schweikert ....... A61M 25/0009 604/28 |
| 6,881,542 | B1 | 4/2005 | Boylan et al. |
| 2002/0141966 | A1 | 10/2002 | Dang |
| 2005/0142163 | A1 | 6/2005 | Hunter et al. |
| 2005/0281883 | A1 | 12/2005 | Daniloff et al. |
| 2006/0009801 | A1 | 1/2006 | McGurk |
| 2006/0052295 | A1 | 3/2006 | Terman |
| 2006/0111754 | A1 | 5/2006 | Rezai et al. |
| 2006/0167416 | A1 | 7/2006 | Mathis et al. |
| 2007/0110813 | A1 | 5/2007 | Ingenito et al. |
| 2008/0172013 | A1* | 7/2008 | Kucklick ................ A61M 5/14 604/288.03 |
| 2013/0102999 | A1 | 4/2013 | Looper et al. |

FOREIGN PATENT DOCUMENTS

| | | |
|---|---|---|
| WO | 2002102994 A2 | 12/2002 |
| WO | 2006026412 A2 | 3/2006 |
| WO | 2009060322 A2 | 5/2009 |
| WO | 2011140449 A2 | 11/2011 |
| WO | 2012161954 A2 | 11/2012 |

OTHER PUBLICATIONS

Tremblay, Alain, MD et al., "Use of a Drug Eluting Pleural Catheter for Pleurodesis," Chest, Oct. 2008, 2 paqes.

International Search Report and Written Opinion for PCT/US2012/059661, dated Feb. 1, 2013, 13 pages.

\* cited by examiner

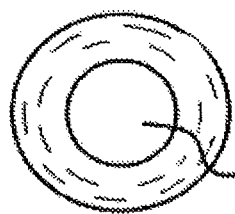 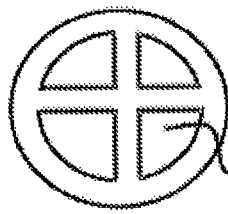 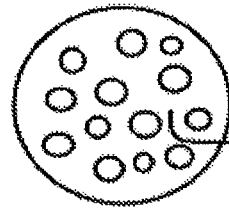
FIG. 2B  FIG. 2C  FIG. 2D
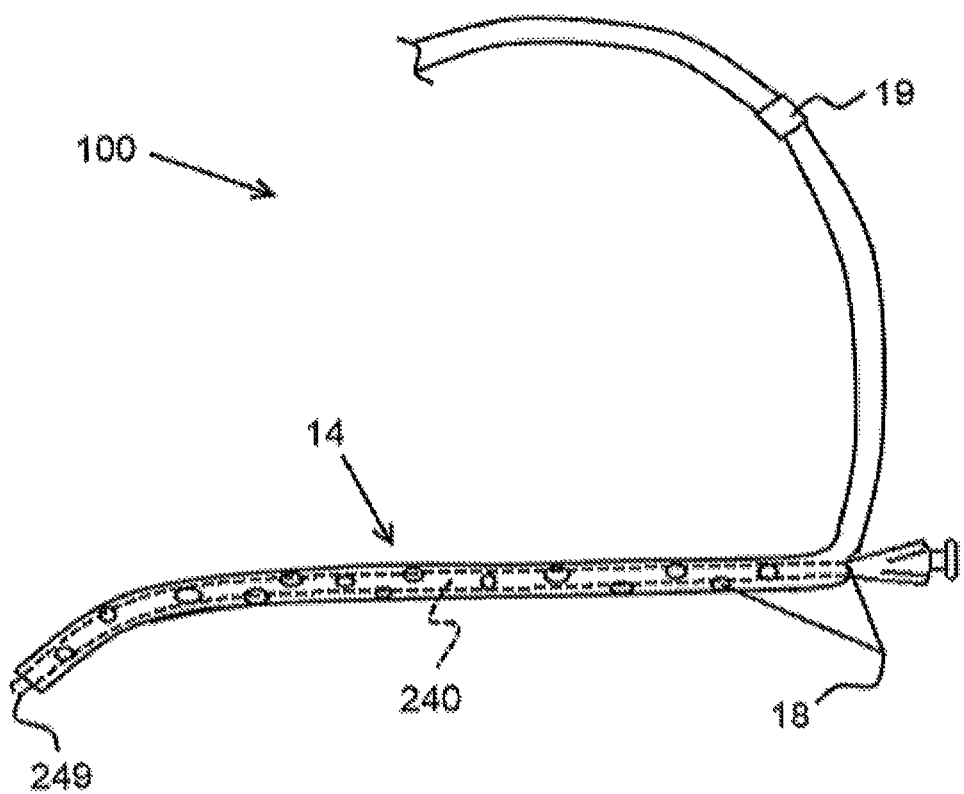
FIG. 3

AUTOLOGOUS PLEURODESIS METHODS AND DEVICES

CROSS-REFERENCE TO RELATED APPLICATIONS

This application is a continuation of U.S. patent application Ser. No. 15/610,381, filed Mar. 31, 2017, which is a continuation of U.S. patent application Ser. No. 14/139,008, filed Dec. 23, 2013, which are incorporated by reference herein in their entirety.

TECHNICAL FIELD

Embodiments of the present invention relate to the field of inducing pleurodesis. More particularly, embodiments of the present invention relate to methods and devices for performing a drainage function and a sclerosis- and/or adhesion-inducing function.

BACKGROUND

Ascites describes an accumulation of fluid and other materials in the peritoneal or other body cavity. Pleural effusion refers to the effusion of fluid into the pleural space. Both excess fluid accumulation conditions may be treated with a drainage apparatus of the type shown in FIG. 1. The apparatus 100 is shown as installed in a patient body and includes a drainage container 114. The drainage container 114 is removably attached by a proximal tube 110 at a valve 60 to a distal catheter 12. The valve 60 may be configured in any number of ways known in the art for attaching catheters together in a fluid-patent manner, (which may include a two-part valve), and the proximal portion attached to the distal catheter 12 may be configured to be self-sealing when disconnected from the proximal tube 110. The proximal end portion of the distal catheter 12 is shown indwelling the patient, disposed through the body wall 21 into an intra-body space 23, which may be—for example—a pleural, peritoneal, or other body lumen. That proximal portion includes a sealing cuff 19 and a flexible fluid-intake length 14 including fenestrations 18, shown in the intra-body space 23. This structure may be better understood with reference to U.S. Pat. No. 5,484,401, which is incorporated herein by reference, and with reference to commercial products marketed under the name PleurX® by CareFusion® of San Diego, Calif.

The pleural space normally contains approximately 5 to 20 ml of fluid. The pH, glucose and electrolytes of the fluid are equilibrated with plasma, but the fluid is relatively protein-free. The fluid is the result of the hydrostatic-oncotic pressure of the capillaries of the parietal pleura. About 80-90% of the fluid is reabsorbed by the pulmonary venous capillaries of the visceral pleura, and the remaining 10-20% is reabsorbed by the pleural lymphatic system. The turnover of fluid in the pleural space is normally quite rapid—roughly 35 to 75% per hour, so that 5 to 10 liters of fluid move through the pleural space each day.

A disruption in the balance between the movement of fluid into the pleural space and the movement of fluid out of the pleural space may produce excessive fluid accumulation in the pleural space. Such disruptions may include, for example, (1) increased capillary permeability resulting from inflammatory processes such as pneumonia, (2) increased hydrostatic pressure as in congestive heart failure, (3) increased negative intrapleural pressure as seen in atelectasis (partial or total lung collapse), (4) decreased oncotic pressure as occurs in the nephrotic syndrome with hypoalbuminemia, and (5) increased oncotic pressure of pleural fluid as occurs in the inflammation of pleural tumor growth or infection. Pleural effusion is particularly common in patients with disseminated breast cancer, lung cancer or lymphatic cancer and patients with congestive heart failure, but also occurs in patients with nearly all other forms of malignancy.

The clinical manifestations of pleural effusion include dyspnea, cough and chest pain which diminish the patient's quality of life. Although pleural effusion typically occurs toward the end of terminal malignancies such as breast cancer, it occurs earlier in other diseases. Therefore relieving the clinical manifestations of pleural effusion is of a real and extended advantage to the patient. For example, non-breast cancer patients with pleural effusion have been known to survive for years.

There are a number of treatments for pleural effusion. If the patient is asymptomatic and the effusion is known to be malignant or paramalignant, treatment may not be required. Such patients may develop progressive pleural effusions that eventually do produce symptoms requiring treatment, but some will reach a stage where the effusions and reabsorption reach an equilibrium that is still asymptomatic and does not necessitate treatment.

Pleurectomy and pleural abrasion is generally effective in obliterating the pleural space and, thus, controlling the malignant pleural effusion. This procedure is done in many patients who undergo thoracotomy for an undiagnosed pleural effusion and are found to have malignancy, since this would prevent the subsequent development of a symptomatic pleural effusion. However, pleurectomy is a major surgical procedure associated with substantial morbidity and some mortality. Therefore, this procedure is usually reserved for patients with an expected survival of at least several months, who are in relative good condition, who have a trapped lung, or who have failed a sclerosing agent procedure.

In general, systemic chemotherapy is disappointing for the control of malignant pleural effusions. However, patients with lymphoma, breast cancer, or small cell carcinoma of the lung may obtain an excellent response to chemotherapy. Another approach to removing fluid from the pleural space has been to surgically implant a chest tube. Such tubes are commonly quite rigid and fairly large in diameter and are implanted by making a surgical incision and spreading apart adjacent ribs to fit the tube into place. Such procedures are painful to the patient, both initially when the chest tube is inserted and during the time it remains within the pleural space.

Thoracentesis is a common approach to removing pleural fluid, in which a needled catheter is introduced into the pleural space through an incision in the chest cavity and fluid is positively drawn out through the catheter using a syringe or a vacuum source. The procedure may also include aspiration utilizing a separate syringe. There are a number of difficulties in thoracentesis, including the risk of puncturing a lung with the catheter tip or with the needle used to introduce the catheter, the risk of collapsing a lung by relieving the negative pressure in the pleural space, the possibility of aggravating the pleural effusion by stimulating fluid production in the introduction of the catheter, and the risk of infection. One of the primary difficulties with ordinary thoracentesis procedures is that fluid reaccumulates in the pleural space relatively quickly after the procedure is performed, and so it is necessary to perform the procedure repeatedly—as often as every few days. Similar techniques and difficulties exist for certain abdominal/peritoneal conditions. However, it would be advantageous to provide improved methods for treating pleural effusions, peritoneal ascites, and other conditions.

BRIEF SUMMARY

In one aspect, embodiments may include methods for introducing a sclerotic agent through a thoracic drainage catheter, a rigid needle, a flexible (including memory-metal) cannula, or other device providing access to a target site in need of treatment. In another aspect, embodiments may provide methods for effecting pleurodesis in an outpatient procedure that may be effected via an indwelling drainage catheter. In other aspects, embodiments may include devices and methods for autologous and non-autologous inducement of pleurodesis.

BRIEF DESCRIPTION OF THE DRAWINGS

FIG. 2A shows a transverse section view of the inner tube along line 2A-2A of FIG. 2;

FIGS. 2B-2D show different distal end tip configurations of the inner tube;

FIG. 3 shows an assembled view of the device of FIG. 2;

DETAILED DESCRIPTION

Figure 1:
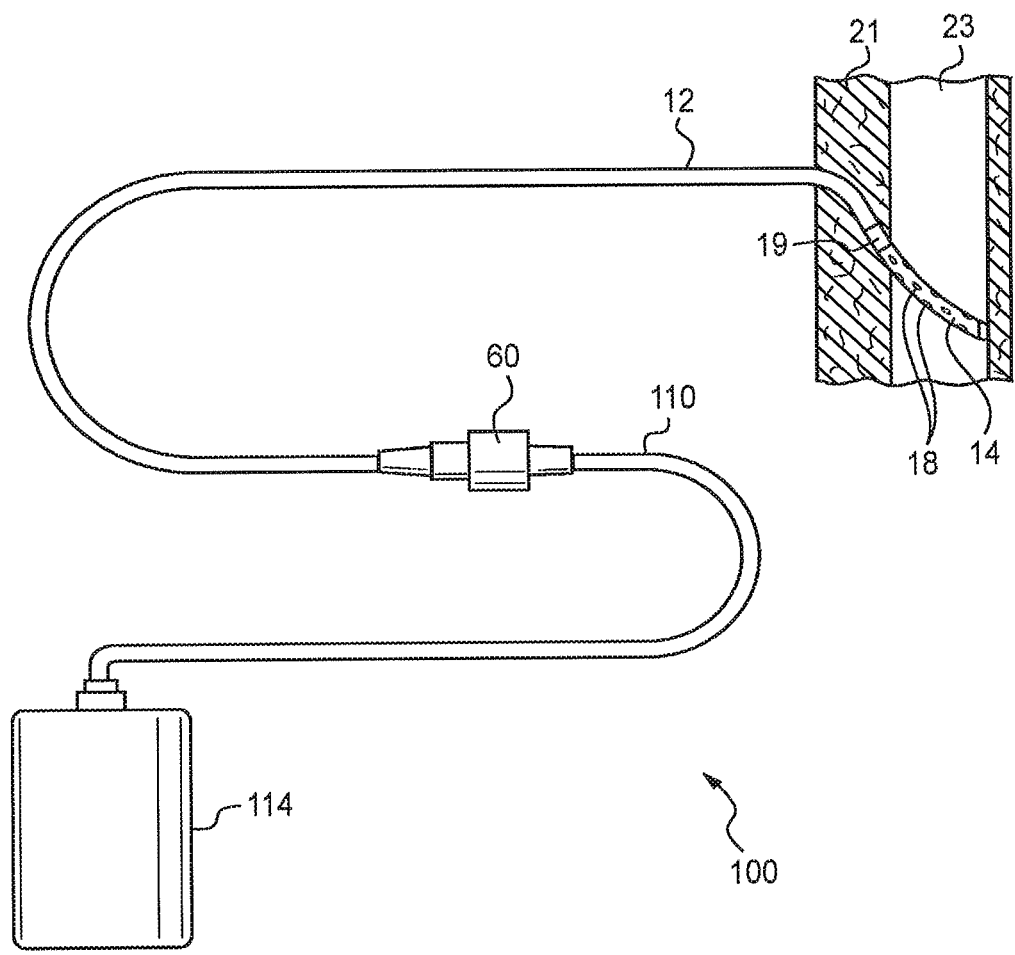
FIG. 1 illustrates a drainage apparatus as known in the prior art.

Embodiments generally are described with reference to the drawings in which like elements are generally referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments of the present invention, such as—for example—conventional fabrication and assembly.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly indicates otherwise. Throughout the specification, the terms "distal" and "distally" shall denote a position, direction, or orientation that is generally away from the physician and/or toward the patient. Accordingly, the terms "proximal" and "proximally" shall denote a position, direction, or orientation that is generally towards the physician and/or away from the patient.

Within a device for accelerating and/or enhancing pleurodesis, it may be desirable to provide a distal indwelling portion of the tube that is coated at least partially with a substance that is intended to be delivered to the body over an extended period of time in a diluted, consistent, and/or titrated manner. One example of such a system maybe a tube body configured for pleurodesis of the pleural space by means of a sclerosing agent such as, for example, silver nitrate. In these instances, it is preferable that the silver nitrate coating in its base/concentrated form not contact the surrounding tissue directly due to its high concentration and potential tissue reactions thereto. The coating most preferably will be eluted or otherwise be released over time from the catheter. Other suitable sclerotic agents may include antimicrobial agents, or other materials configured for inducing pleurodesis (e.g., polyvinylpyrrolidone (PVP), talc (e.g., as a slurry), bleomycin, mitoxantrone, mitomycin, thiotpea, cytarabine, quinacrine, tetracycline (defined herein to include tetracycline derivative such as doxycycline and minocycline), OK432 (*Streptococcus pyogenes* type A3), SSAg (*Staphylococcus aureus* superantigen), fibrin glue, povidone iodine (PVP-I), autologous "blood patch," or any combination thereof).

Modern pleural and peritoneal drainage systems have made it possible for patients to use devices like those illustrated in FIG. 1 to conduct drainage on periodic office or hospital visits. For patients who experience recurrent effusions, repeat drainage procedures at a clinical facility can be avoided by the installation of an indwelling tunneled catheter that can be drained at home. In addition, for some patients it may be desirable to administer a substance or provide a therapeutic intervention to the area where the catheter is inserted. For example, in patients with pleural effusion who have a lung that re-expands upon drainage, fusion of the visceral and parietal pleura is a treatment option that eliminates at least a portion of the pleural cavity and thus eliminates the space where the fluid accumulates. This procedure is called pleurodesis and can be accomplished through draining the effusion and inciting the patient's foreign body response. Mechanical or chemical means can be used to cause the irritation. In other instances, continuous delivery of medication or cell signaling molecules may be desired in the area where the catheter resides.

Chemical pleurodesis may use irritants and/or antibiotic materials (also known as sclerotic/sclerosis agents) that may also provide mechanical irritation to trigger cell growth and/or resist infection. Examples of materials known and used include bleomycin, tetracycline, and povidone iodine. As another example, a slurry of talc can be introduced into the pleural space. The instilled chemicals cause irritation between the parietal and the visceral layers of the pleura which closes off the space between them and prevents further fluid from accumulating. Chemical pleurodesis may be a painful procedure, so patients are often premedicated with a sedative and analgesics. A local anesthetic may be instilled into the pleural space, or an epidural catheter may be placed for anesthesia. Generally, to be effective, introduction of structures and materials for pleurodesis desirable will create irritation and then keep the space dry. In order to establish pleurodesis, it is preferable that the parietal and visceral layers of the pleura remain in juxtaposition. As such, it is preferable that when mechanical and/or chemical irritation is complete a drainage tube will remain in place to remove the fluid over the time it takes for the adhesion accomplishing pleurodesis to occur. Certain structures and methods for delivering sclerosis agents are disclosed in U.S. App. Pub. No. 2013/0102999 to Looper, et al., which is incorporated herein in its entirety.

Chemical pleurodesis generally is currently performed in one of two ways: 1) The sclerotic pleurodesis agent is introduced through a chest tube into the pleural space, or 2) The agent is introduced during a video assisted thoracoscopy (VATS) procedure while the patient is under general anesthesia. Because both methods require use of a chest tube, the patient is required to stay in the hospital for up to one week until the effusion resolves. At present, no outpatient procedures or indwelling catheters are known to be used in the instillation of sclerosing agents. As such, it would be useful to provide methods for effecting pleurodesis on a less-invasive basis, including in an outpatient procedure that may be effected via an indwelling drainage catheter.

Figure 2:
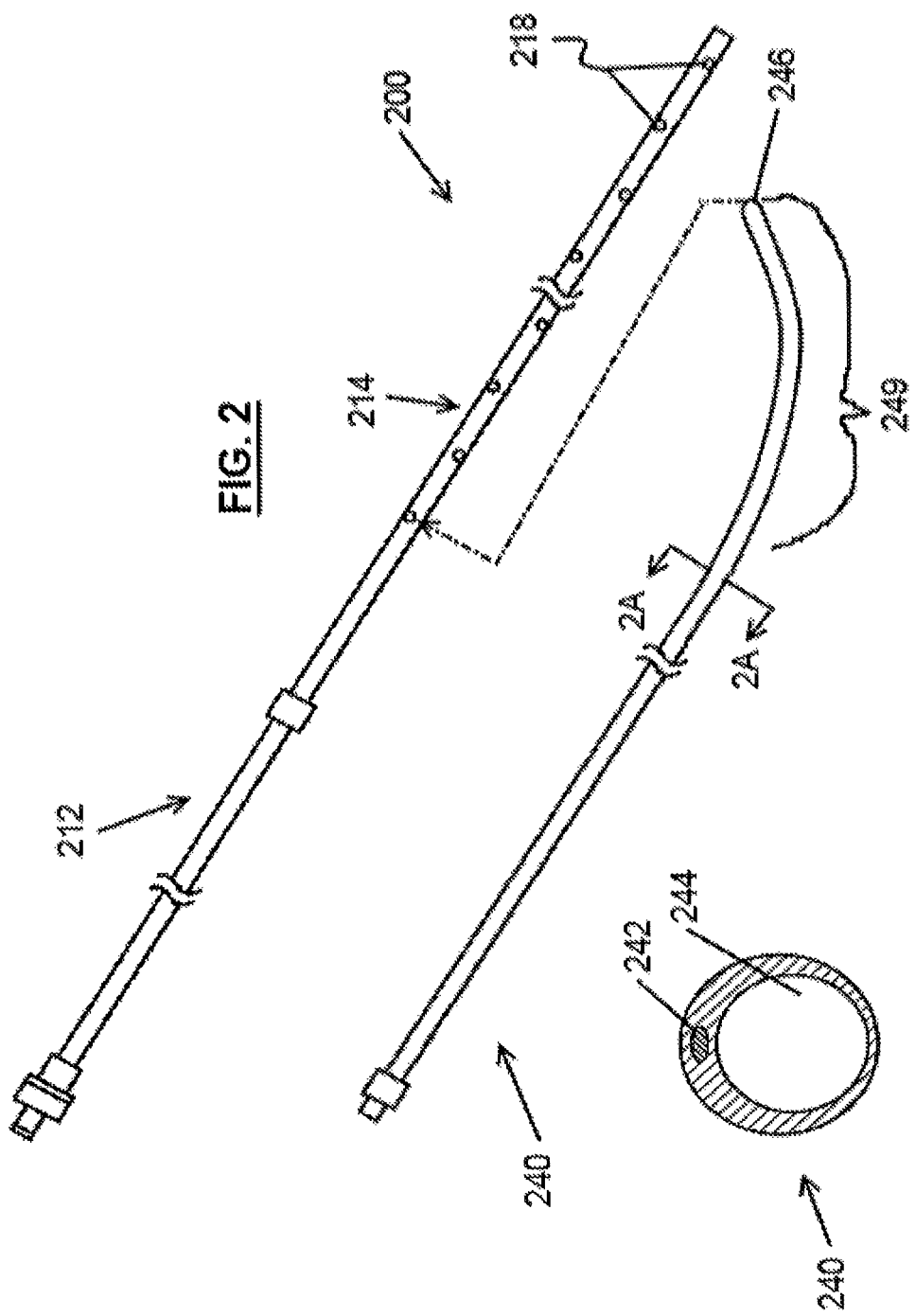
FIG. 2 shows an assembly view of a device including an outer tube configured as a drain tube and a curved inner tube (which may be curved by a memory-material)

Main components of an injection catheter assembly 200 and methods for facilitating pleurodesis, or another sclerosis-inducement procedure, are described with reference to FIGS. 2-4C. FIG. 2 shows a disassembled view, including an elongate flexible outer tube body 212 including a distal length 214 configured to indwell a patient body trunk cavity. The outer tube body 212 includes at least one body lumen extending longitudinally through at least a lengthwise portion of the distal length, where the lumen substantially defined by an inner diameter surface of the tube body (internal lumen not shown, and may include a plurality of lumens as multi-lumen tube construction is well-characterized in the art). The outer tube body 212 shown is generally configured as a drainage tube with fenestrations 218, which are configured to facilitate drainage from a body cavity.

The assembly 200 includes a flexible, curved inner cannula body 240, which is dimensioned for passage through the body lumen of the outer tube body 212. The inner cannula body 240 may include a memory-material 242 imposing a pre-determined curve along a length 249 of the inner cannula body 240, or may otherwise maintain a curve. The inner cannula body 240 also includes an injection lumen 244 and at least one distal-region opening 246 configured for dispensing a medicament. The memory-material 242 and the injection lumen 244 are shown more clearly in FIG. 2A, which provides a magnified transverse section view along line 2A-2A of FIG. 2. The inner and/or outer surfaces of the inner cannula body 240 and the outer tube body 212 may include includes a lubricious coating configured to resist adhesion by a medicament. Memory material may include any appropriate metallic or polymeric material upon which shape-memory may be imposed, while allowing flexibility. For example, various nitinol and other memory metal compounds are well-known and commonly used in the medical device art. Other materials are known in the art that can receive and default-return to a shape (imposed by mechanical, temperature, and/or other means) after flexure into different shape(s). The memory configuration may be assumed based upon temperature, release of constraint, and/or by active means, as known in the art for different materials.

Medicaments dispensable through the assembly 200 may include sclerosis-inducing agent(s), therapeutic agent(s), chemotherapy agent(s), gene therapy agent(s), and/or other materials, introduced by syringe, infusion pump, or other means. The medicaments may be configured as liquids, solutions, suspensions, gels, pastes, or any combination thereof and may include effervescent material (e.g., sodium bicarbonate and citric acid or other combination that can be activated by temperature, liquid-contact, or other means) configured to aid dispersion through the body cavity by formation of bubbles and/or spreading by similar means. Examples of medicaments may include talc, silver nitrate, bleomycin, and/or other sclerosis-inducing agents. In addition or in the alternative, examples of medicaments may include chemotherapy agents, antibiotic(s), loculation-breakup compound(s) (e.g., tissue plasminogen activator tPA), and/or other materials, which may be introduced after the assembly is placed in a patient body, or which may be pre-loaded into the injection lumen 244 before the inner cannula is fully engaged into the outer tube 212. Each medicament or combination of medicaments may be provided as, or include additives to be rendered, radiopaque and/or more highly and contrastingly ultrasound-reflective to enhance visibility with medical imaging means.

A removable structure such as, for example, a stylet (not shown) may be used to block and/or seal the injection lumen of the inner cannula 240. The inner cannula body 240 may include one or more one visualization markers configured to be visualizable in a patient body by at least one of fluoroscopy, ultrasound, magnetic resonance imaging, and computed tomography. This feature may assist treating personnel during a procedure for introducing a medicament through the inner cannula 240.

FIGS. 2B, 2C, and 2D show tip configurations that may provide for desirable dispensing patterns for directing a selected medicament. FIG. 2B shows an end-on view of an open tip 249a of an inner cannula, which opening is configured to emit a stream or otherwise generally unimpeded flow of medicament. FIG. 2C shows an end-on view of a segmented-opening tip 249b of an inner cannula, which opening is configured to emit a plurality of streams or coarse spray of medicament. FIG. 2D shows an end-on view of a multi-aperture tip 249c of an inner cannula, which opening is configured to emit a spray of medicament.

FIG. 3 shows an inner cannula 240 assembled to a drainage apparatus 100. In this embodiment, the inner cannula 240 is shown as having been inserted through one of the fenestrations 18. In the illustrated embodiment, the fenestration 18 is the one nearest the cuff 19. In certain embodiments, a hub, port, or other structure may be provided on a drainage apparatus 100 (e.g., a Touhy-Borst valve or other construct, not shown) for effective access by an inner cannula 240. The distal end 249 of the inner cannula 240 extends beyond the distal end 17 of the distal length 14 of the drainage apparatus 100, and may extend through a valve (e.g., like valve 60 of FIG. 1).

Figure 4A:
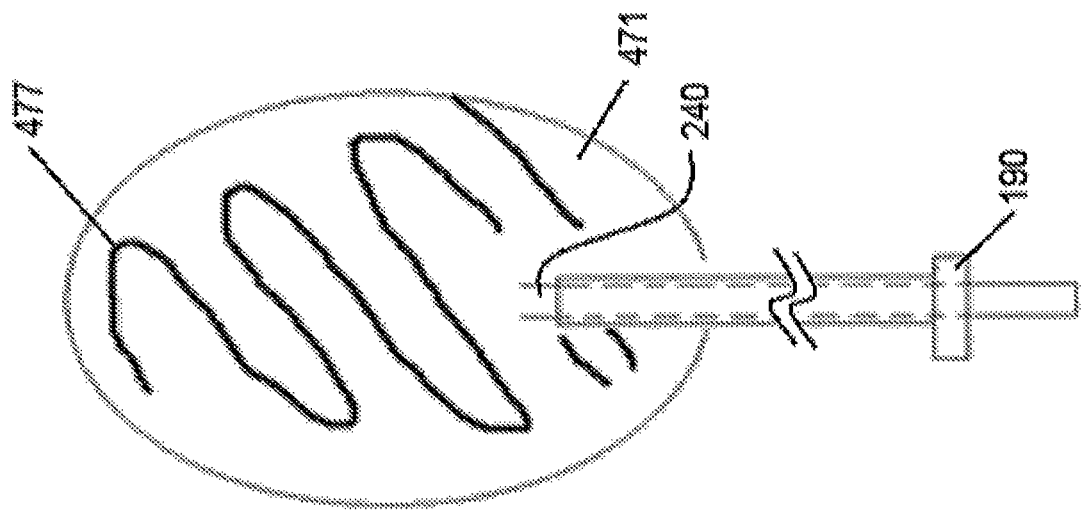
FIGS. 4A-4C show a method of dispensing a medicament.
Figure 4B:
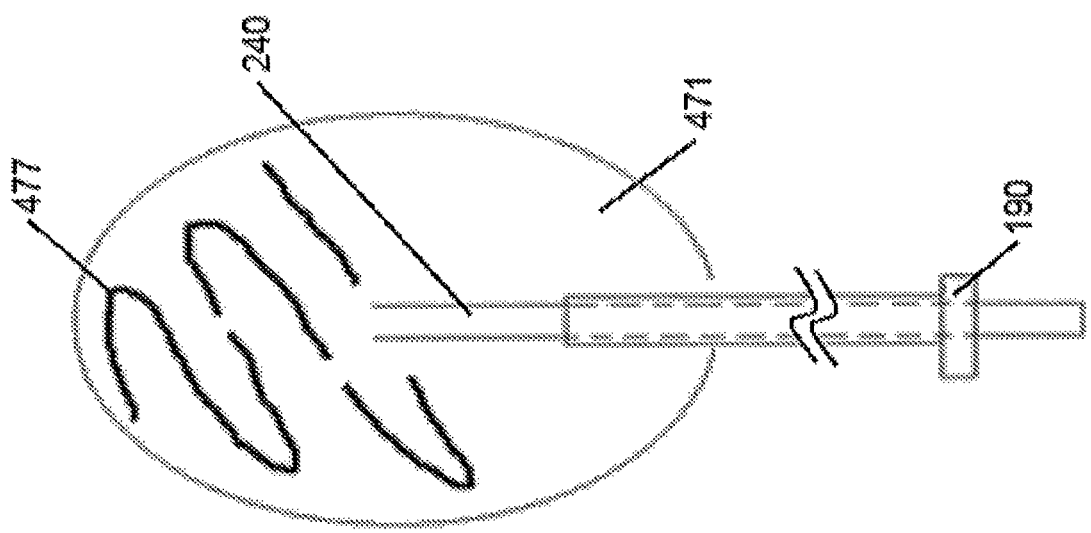
Figure 4C:
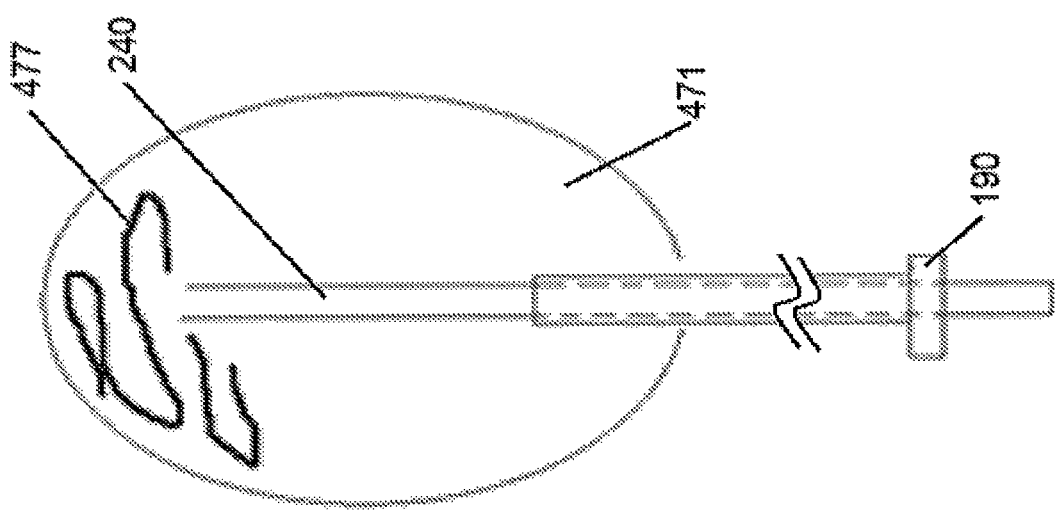

FIGS. 4A-4C show, in simplified/diagrammatic form, a method of use for an inner cannula 240. The inner cannula 240 may be assembled to a drainage apparatus 100 as shown in FIG. 3, and/or it may be directed through a valved introducer 190. The distal tip 249 of the inner cannula 240 is directed to adjacent a target region 471 (e.g., a location in the pleural space). In the illustrations, a drainage catheter 412 is shown as having been directed through the valved introducer 190. Then, as shown in FIG. 4A, a medicament (such as—for example—a talc-containing material) 477 is directed onto a surface of the target region 471. The material 477 may be distributed in a continuous manner or pattern, or in a staggered discontinuous manner or pattern, and shown in FIG. 4B, where the inner cannula 240 has been retracted along its axis and/or otherwise manipulated during dispensing of the material 477. The material 477 may be directed from and through any appropriate injection system, such as—for example—a syringe, a pressurized injector, or any other appropriate means for injection, as will be apparent to those skilled in the art.

In preferred embodiments, the pattern or other distribution of material 477 may be performed in a manner to promote desired adhesion by location of placement. As known in the art, the material 477 will generally generate a bodily response to mechanical and/or chemical irritation that promotes adhesion. The adhesion is desirable to decrease or eliminate an undesired space (e.g., pleural effusion). This method may also be effected with any apparatus described below with reference to FIGS. 5 and 6.

A patient's own blood (or compatible blood or blood components) may be effective to provide or enhance therapeutic treatment of a pleural effusion or other condition being treated with a method and/or apparatus of the present disclosure, and may therefore be considered as a medicament in the present disclosure. In another embodiment, described here with reference to FIG. 5, a method and apparatus may be provided for autologous blood transfer to the target region. A catheter 512 configured to partially indwell a patient in the manner of catheters 12 described above (and including the structure disclosed there) is provided with a valve 560 connecting the catheter 512 in fluid communication with tubing 587. An opposite end of the tubing 587 may be placed in fluid communication with an autologous or other blood supply 589 (shown diagrammatically only; e.g., a patient's own vein via an intravenous needle, a container of autologous or otherwise compatible whole blood or blood components), which blood supply may further include structure providing supply of a medicament other than blood or blood component(s). A shunt or pump 588 may be provided to facilitate blood flow to and through the tubing 587, valve 560, and catheter 512. The interior surface(s) of the tubing 587, shunt or pump 588 (if present), valve 560, and/or catheter 512 may be coated with a lubricious material and/or an anti-clotting agent (e.g., heparin) to lessen/minimize the possibility of the blood clotting or adhering to those surfaces. The tubing 587 may be removed and replaced with a vacuum bottle or other drainage modality (not shown) when desired to effect drainage of the region indwelt by the catheter 512.

Figure 5:
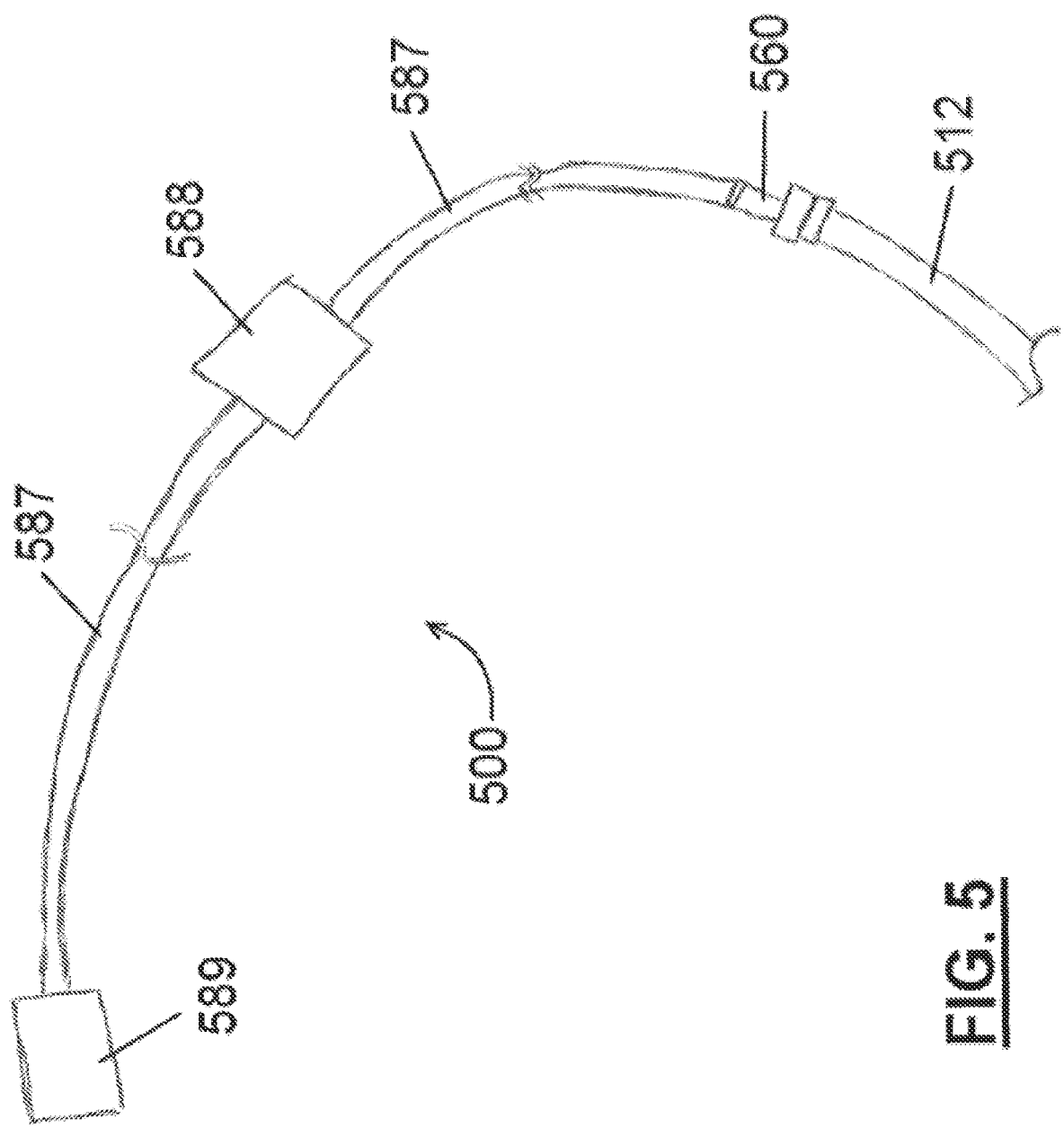
FIG. 5 shows a device and method for autologous or other blood infusion.
Figure 6:
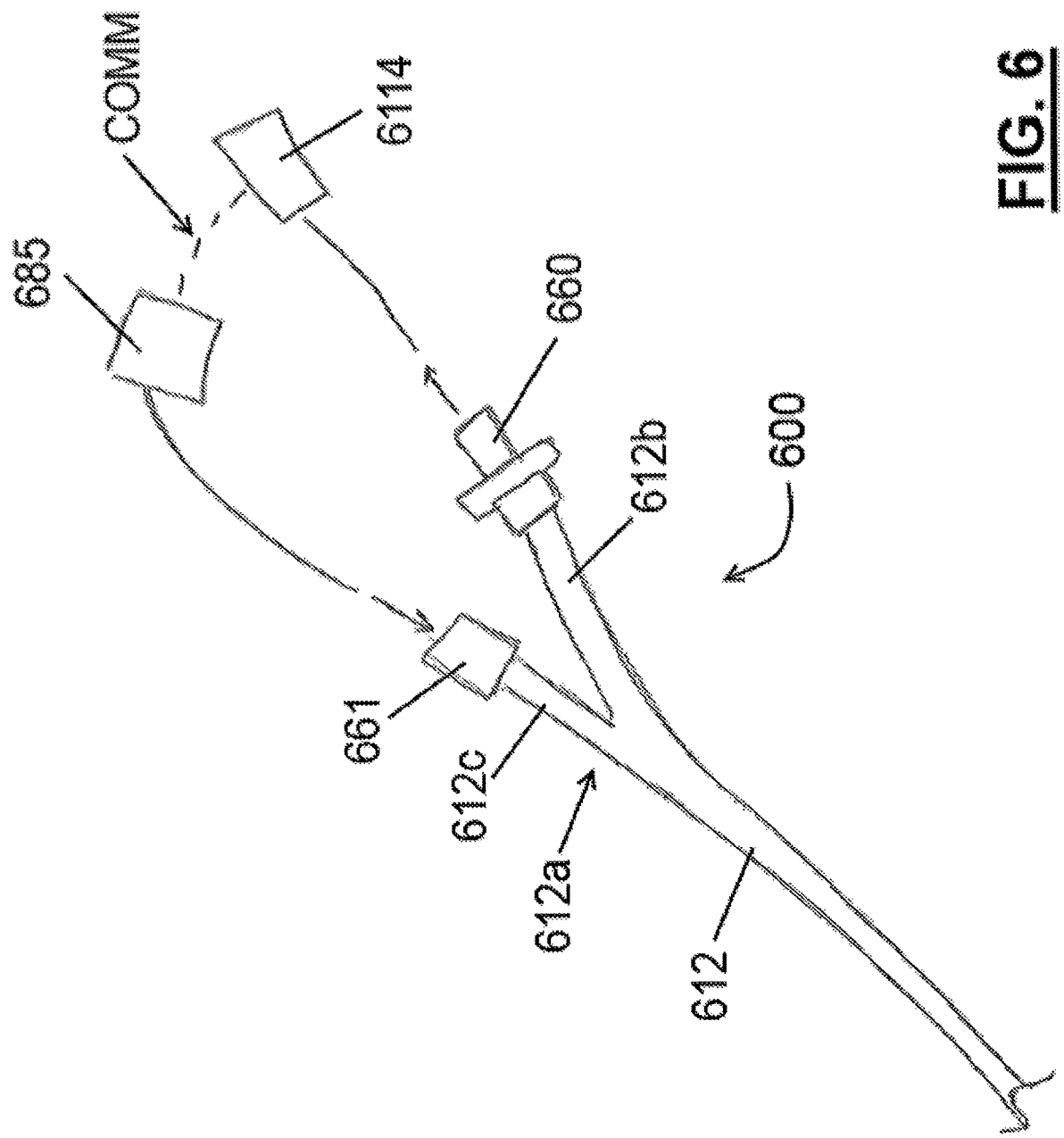
FIG. 6 shows a split-catheter embodiment for infusion and drainage.

A different apparatus embodiment for effecting the method described with reference to FIG. 5 is shown in FIG. 6. A catheter 612 configured to partially indwell a patient in the manner of catheters 12 described above (and including the structure disclosed there) is provided, including a Y-type split region 612a that provides a plurality of tube lumens along a length of the device, where the plurality of lumens (preferably two, but more possible as noted with reference to FIGS. 2C-2D) continues through the unitary unsplit length. A first branch 612b is provided with a valve 660 configured to interface with a vacuum bottle or other drainage modality 6114 (e.g., via a drainage tube, not shown, like the tube 110 described above, where drainage modalities are well-known in the art including an in-wall suction/vacuum unit and other drainage structures and/or mechanisms). The other branch 612c may include a dripless valve 661 configured to interface with an infusion assembly 685 (shown only diagrammatically) which may include a syringe, infusion pump, autologous blood supply, and/or other means for supplying a medicament or other desired material for infusion via the catheter 612. The infusion assembly 685 may be placed in communication with the drainage modality 6114 in a manner providing for coordinated infusion and drainage via the catheter 660. The communication may be electrical, mechanical, fluid/vacuum-based, or via any other means appropriate for effecting desired coordination of infusion and drainage.

Those of skill in the art will appreciate that embodiments not expressly illustrated herein may be practiced within the scope of the present invention, including that features described herein for different embodiments may be combined with each other and/or with currently-known or future-developed technologies (including specifically combining the features of the different embodiments shown and described in the drawing figures, such as providing distal structure and function shown and discussed with reference to FIGS. 2-4C with the embodiments of FIGS. 5-6, where the distal structure is not explicitly illustrated), while remaining within the scope of the claims presented here. For example, the various physical structures disclosed may also provide mechanical irritation promoting a desired sclerotic effect, and the structures and components disclosed herein may be combined with each other or other features. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

We claim:

1. A catheter assembly configured for drainage and for blood-induced pleurodesis inducement, the assembly comprising:
    an elongate flexible first tube body comprising a distal length configured to indwell a patient body trunk cavity from and distal of a sealing cuff that is configured to contact sealingly with a patient's body wall;
    at least one first tube body lumen extending longitudinally through a lengthwise portion of the distal length, the at least one first tube body lumen substantially defined by an inner diameter surface of the first tube body;
    the distal length including at least one fenestration providing fluid communication between the first tube body lumen and a region external of the first tube body;
    wherein the at least one first tube body lumen comprises a plurality of lumens that extend through a length of the first tube body, with at least one lumen configured for medicament infusion and at least one lumen configured for drainage, the first tube body comprising the distal length that is unitary and unsplit and a split region that splits the first tube body into at least two branches such that the first tube body forms the split region, the distal length and the at least two branches, wherein the at least one lumen configured for medicament infusion extends through one of the at least two branches and the at least one lumen configured for drainage extends through another of the at least two branches;
    a first valve connected to the one of the at least two branches in communication with the at least one lumen configured for drainage, the first valve configured to interface with a drainage modality; and
    a second valve connected to the another of the at least two branches and in communication with the at least one lumen configured for medicament infusion, the second valve configured to interface with an infusion assembly.

2. The catheter assembly of claim 1, wherein at least one portion of the distal length is configured as an injection portion that includes at least one surface and/or a further opening constructed to permit passage therethrough of a sclerotic agent.

3. The catheter assembly of claim 1, wherein, in a first state, a second tube body is removably attached to the second valve at a distal end of the second tube body, and in the first state, a proximal end of the second tube body is disposed in fluid communication with a blood supply.

4. The catheter assembly of claim 3, wherein, in a second state, the proximal end of the second tube body is not disposed in fluid communication with a blood supply.

5. The catheter assembly of claim 4, wherein, in a third state, a vacuum bottle or other drainage modality is attached in fluid communication with the first tube body using the first valve.

6. A catheter assembly apparatus for autologous blood transfer to a target region within a patient's body, the apparatus comprising:
   a drainage modality configured for receiving fluid from the patient's body;
   an infusion assembly configured for supplying a medicament to the patient's body;
   a catheter assembly comprising:
      an elongate flexible first tube body comprising a distal length configured to indwell a patient body trunk cavity from and distal of a sealing cuff that is configured to contact sealingly with a patient's body wall;
      at least one first tube body lumen extending longitudinally through a lengthwise portion of the distal length, the at least one first tube body lumen substantially defined by an inner diameter surface of the first tube body;
      the distal length including at least one fenestration providing fluid communication between the first tube body lumen and a region external of the first tube body;
      wherein the at least one first tube body lumen comprises a plurality of lumens that extend through a length of the first tube body, with at least one lumen configured for medicament infusion and at least one lumen configured for drainage, the first tube body comprising the distal length that is unitary and unsplit and a split region that splits the first tube body into at least two branches such that the first tube body forms the split region, the distal length and the at least two branches, wherein the at least one lumen configured for medicament infusion extends through one of the at least two branches and connects to the infusion assembly and the at least one lumen configured for drainage extends through another of the at least two branches and connects to the drainage modality;
      a first valve connected to the one of the at least two branches in communication with the at least one lumen configured for drainage, the first valve configured to interface with the drainage modality; and
      a second valve connected to the another of the at least two branches and in communication with the at least one lumen configured for medicament infusion, the second valve configured to interface with the infusion assembly.

7. The apparatus of claim 6, wherein at least one portion of the distal length is configured as an injection portion that includes at least one surface and/or a further opening constructed to permit passage therethrough of a sclerotic agent.

8. The apparatus of claim 7, wherein, in a first state, a second tube body of the catheter assembly is removably attached to the second valve at a distal end of the second tube body, and in the first state, a proximal end of the second tube body is disposed in fluid communication with a blood supply.

9. The apparatus of claim 8, wherein, in a second state, the proximal end of the second tube body is not disposed in fluid communication with a blood supply using the first valve.

10. A method of delivering a medicament via a catheter assembly in a body lumen, the method comprising:
    directing a distal portion including the distal length of the first tube body of the catheter assembly of claim 1 into a body cavity;
    directing the distal portion to a target site;
    dispensing the medicament to the target site through the at least one lumen configured for medicament infusion.

11. The method of claim 10, wherein the medicament comprises one or more of a sclerosing agent, a therapeutic agent, an effervescent material, a radiopaque material, whole blood and blood components.

12. The method of claim 10, wherein the first tube body comprises a lubricious coating configured to resist adhesion by a medicament.

13. The method of claim 10 further comprising connecting the first valve to the at least one lumen configured for drainage.

14. The method of claim 10 further comprising connecting the second valve to the at least one lumen configured for medicament infusion with an infusion assembly.

* * * * *